United States Patent
Soukos et al.

(10) Patent No.: US 7,332,200 B1
(45) Date of Patent: Feb. 19, 2008

(54) PERMEABILIZING BIOFILMS

(75) Inventors: Nikolaos S. Soukos, Revere, MA (US); Shun Lee, Arlington, VA (US); Apostolos G. Doukas, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/019,837

(22) PCT Filed: May 12, 2000
(Under 37 CFR 1.47)

(86) PCT No.: PCT/US00/13231

§ 371 (c)(1),
(2), (4) Date: Sep. 10, 2002

(87) PCT Pub. No.: WO00/67917

PCT Pub. Date: Nov. 16, 2000

Related U.S. Application Data

(60) Provisional application No. 60/133,730, filed on May 12, 1999.

(51) Int. Cl.
*B05D 3/06* (2006.01)
(52) U.S. Cl. .................................. 427/554
(58) Field of Classification Search ............ None
See application file for complete search history.

(56) References Cited

U.S. PATENT DOCUMENTS

| | | | |
|---|---|---|---|
| 5,421,816 A | 6/1995 | Lipkovker | 604/20 |
| 5,614,502 A * | 3/1997 | Flotte et al. | 514/34 |
| 5,618,275 A | 4/1997 | Bock | 604/290 |
| 5,656,016 A * | 8/1997 | Ogden | 601/2 |
| 5,722,397 A | 3/1998 | Eppstein | 128/633 |
| 5,885,211 A | 3/1999 | Eppstein et al. | 600/309 |
| 6,009,346 A | 12/1999 | Ostrow | 604/20 |
| 6,030,374 A | 2/2000 | McDaniel | 604/506 |
| 6,041,252 A | 3/2000 | Walker et al. | 604/20 |
| 6,352,506 B1 * | 3/2002 | Eppstein et al. | 600/309 |
| 6,573,491 B1 * | 6/2003 | Marchitto et al. | 250/251 |

FOREIGN PATENT DOCUMENTS

WO    WO 98/23325    * 6/1998

OTHER PUBLICATIONS

Flotte et al, Proceedings of the SPIE, 2681, pp. 160-166, 1996.*
Flotte et al, Proceedings of the SPIE, 2391, pp. 202-207, 1995.*
McAuliffe et al, Lasers in Surgery and Medicine, 20, pp. 216-222, 1997.*

(Continued)

*Primary Examiner*—Erma Cameron
(74) *Attorney, Agent, or Firm*—Fish & Richardson P.C.

(57) ABSTRACT

Methods for permeabilizing biofilms using stress waves are described. The methods involve applying one or more stress waves to a biofilm, e.g., on a surface of a device or food item, or on a tissue surface in a patient, and then inducing stress waves to create transient increases in the permeability of the biofilm. The increased permeability facilitates delivery of compounds, such as antimicrobial or therapeutic agents into and through the biofilm.

26 Claims, 2 Drawing Sheets

OTHER PUBLICATIONS

Nigri et al, Lasers in Surgery and Medicine, 29, pp. 448-454, 2001.*
Abstract of Denstedt et al, Journal of Endourology, 12(6), pp. 493-500, 1998.*
Doukas et al, Ultrasound in Medicine and Biology, 22(2), pp. 151-154, 1996.*
Sarkar et al, J. Periodont. Res., 28, pp. 204-210, 1993.*
Qian et al, Colloids and Surfaces: Biointerfaces, 9, pp. 239-245, 1997.*
Costerton et al., "Mechanism of Electrical . . . ," Antimicrobial Agents and Chemotherapy, 38(12):p. 2803-2809, Dec. 1994.
Henry et al., "Phototoxicity of argon laser . . . ," Journal of Photochemistry and Photobiology B: Biology, 34:123-128, 1996.
Sadoudi et al., "Elimination of adhering . . . ," Letters in Applied Microbiology, 24:177-179, 1997.
Soukos et al., "Photomechanical Drug Delivery . . . ," Pharmaceutical Research, 17(4):405-409, 2000.
Sved et al., "The bactericidal effects . . . ," J. Clin. Periodontol., 24:432-439, 1997.
Wellman et al., "Bacterial Biofilms . . . ," Antimicrobial Agents and Chemotherapy, 40(9):2021-2014, Sept. 1996.
Wilson et al., "Killing of *streptococcus* . . . ," Journal of Antimicrobial Chemotherapy, 37:377-381, 1996.
Wimpenny, J.W.T., "Validity of Models" Adv Dent Res 11(1):150-159, Apr. 1997.
O'Leary, R., et al. "The bactericidal effects of . . . " J Clin Periodontol, v. 24: 432-439, Jun. 1997.

* cited by examiner

PERMEABILIZING BIOFILMS

RELATED APPLICATIONS

This application claims the benefit of the May 12, 2000 filing date of PCT/US00/13231, filed May 12, 2000, which claims the benefit of the May 12, 1999 priority date of U.S. Provisional Application 60/133,730.

FEDERALLY SPONSORED RESEARCH OR DEVELOPMENT

The U.S. Government may have certain rights in this invention pursuant to Grant No. DE-FG02-91ER61228 awarded by the U.S. Department of Energy.

FIELD OF THE INVENTION

This invention relates to methods of permeabilizing biofilms, e.g., to deliver compounds such as antibiotics, antiseptics or photosensitizing agents into or through biofilms using stress or pressure waves.

BACKGROUND OF THE INVENTION

Most microbial infections in the body are caused by bacteria growing in biofilms composed of single or multiple bacterial species. Biofilms are typically matrix-enclosed microbial aggregates associated with each other and a solid surface. Bacteria within biofilms have an increased resistance to antimicrobial agents relative to that of planktonic cells of the same species. The relative impermeability of biofilms to compounds such as antimicrobial agents may be one reason why microbial infections associated with biofilms are difficult to treat.

SUMMARY OF THE INVENTION

The invention is based on the discovery that stress or pressure waves can be used to permeabilize biofilms, and thus can be used to transport compounds into or through biofilms. The new methods can be used to deliver compounds of a wide range of sizes and net charges into and through biofilms.

In general, the invention features a method of delivering a compound into or through a biofilm. The method includes contacting the biofilm with the compound and propagating a sufficient number of stress waves into the biofilm to increase the permeability of the biofilm, thereby enabling the compound to pass into the biofilm. Because the permeability is enhanced for up to several minutes, the stress wave can be applied in a first step, and the compound can be applied to the permeabilized biofilm in a later step. The later step can be separated by several seconds or minutes from the first step. Alternatively, the stress waves can be used to help drive the compound into the biofilm.

Stress or pressure waves (or impulse transients) are broadband compressive waves having a rise time of at least 500 ps to 100 µs, e.g., 1 ns to 1 µs, 10 ns to 100 ns, 10 ns to 10 µs, or 100 to 300 ns. Stress waves have no measurable tensile component. The stress waves have a peak pressure of at least 50 bar, e.g., 200-700, 300-500, or 550-650 bar. Preferably, the stress waves have a peak pressure of no more than 800, 1000, or 2000 bar. The stress waves have a quick rise time of 10 µs or less, and have a duration of 100 ns to 1 µs, e.g., 200-600 ns. Between 1 and 50 or more pulses (i.e., individual stress waves) can be applied in one treatment, e.g., 1, 2, 3, 4, or 5-10 pulses.

In some embodiments, the stress waves are generated by directing a pulsed laser beam to a target material that is coupled to the biofilm. The laser beam typically has a wavelength of between 140 nm and about 12 µm, e.g., 250, 400, 450, 500, 550, 625, 675, 725, 800, 900, 1000, or 1100 nm. The target material includes a material that absorbs laser energy, and laser-induced rapid heating of the absorbing material generates the stress wave. The target material can be, e.g., a polymer, such as polystyrene. The target material can also be a metal foil. Metals suitable for use in the metal foil include, e.g., aluminum or copper.

In certain embodiments, a material that is transparent to light, e.g., a quartz or glass plate, is bonded to a surface of the target material to confine the plasma generated by a laser beam, thereby increasing the efficiency of conversion of laser energy into the mechanical energy of the stress wave.

For some applications, the compound is provided in a reservoir containing a coupling medium suitable for mixing with the compound. The reservoir is arranged to enable the coupling medium to directly contact a surface of the biofilm. The coupling medium may also contain a surfactant, such as sodium lauryl sulfate.

The biofilm can be associated with an enamel surface of a mammal, e.g., on a tooth surface. The biofilm can also be associated with a periodontal pocket in a mammal. In other embodiments, the biofilm is associated with a tracheal or lung surface.

The compound can be a bioactive agent, e.g., a therapeutic agent such as an antimicrobial agent. Examples of antimicrobial agents include antibiotics, e.g., metronidazole and minocycline; antiseptics, e.g., chlorhexidine and triclosan; photosensitizing agents, e.g., the benzoporpherene derivative monoacid ring A (BPD-MA).

Biofilms that can be permeabilized with the methods of the invention include those produced by a bacteria or a product of a bacteria, e.g., a capsular polysaccharide produced by a bacteria. The biofilm may contain one or several different bacterial species. In some applications the bacterial species will include *P. gingivalis* or *Actinomycete* spp., e.g., *A. viscosus*. The biofilms may also include one or more fungal or protozoan species, or products thereof.

The invention also includes a method of delivering a compound, such as an antimicrobial agent, into or through a biofilm. The method includes contacting the biofilm with the antimicrobial agent and exposing a target material coupled to the biofilm to a pulsed laser beam. One or more stress waves are then propagated through the biofilm contacting the antimicrobial agent, thereby causing the antimicrobial agent to pass into or through the biofilm.

Also included in the invention is a method of permeabilizing a biofilm by exposing the biofilm to stress waves, thereby permeabilizing the biofilm. Thereafter, compounds can pass through the biofilm, e.g., by diffusion or an applied force.

The invention further includes a method of treating disorders associated with a biofilm by exposing the biofilm to a stress wave. In some embodiments, the stress waves permeabilize the biofilm to allow entry by a therapeutic agent. The stress waves can also permeabilize the biofilm to enable entry of other agents, e.g., atmospheric oxygen.

The methods described herein can be applied to biofilms in any animal or human subject, e.g., a mammal such as a human, dog, horse, cow, or cat. The methods are particularly suitable for permeabilizing biofilms associated with diseases of the oral cavity, e.g., chronic destructive periodontitis. The methods can also used to permeabilize biofilms adhering to other solid surfaces not found in an animal, e.g., solid surfaces on instrumentalities used in food processing and in medical applications.

Permeabilizing a biofilm with stress waves allows compounds, such as bioactive agents and therapeutic agents, to be administered with highly localized effects to areas of diseased cells, thus sparing other tissues of the body. In this way, healthy tissues and organs are spared from adverse effects of a systemically administered drug.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

DETAILED DESCRIPTION

Figure 1:
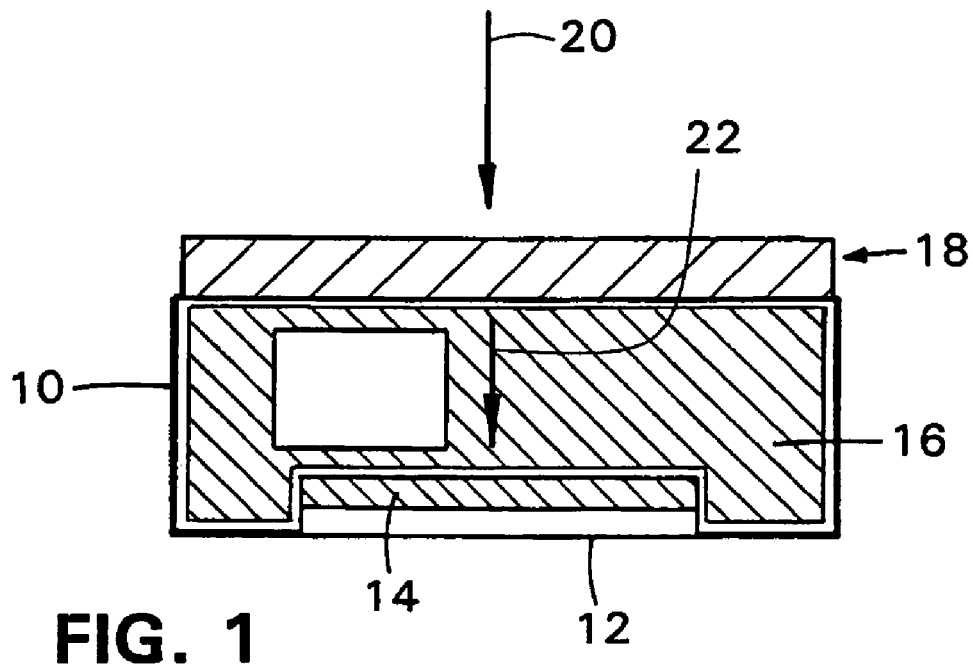
FIG. 1 is a schematic drawing of a device for generating a stress wave by laser ablation of a target coupled to a biofilm.

The invention provides new methods of delivering compounds, e.g., antimicrobial agents such as antibiotics, antiseptics, and photosensitizers, into or through biofilms using stress or pressure waves. The stress waves induce a transient increase in the permeability of the biofilm, thereby allowing delivery of the compound into the biofilm at the time the stress waves are applied, or shortly thereafter. The method is thus useful for delivering compounds to treat conditions associated with the presence of biofilms.

Biofilms are matrix-enclosed microbial aggregates associated with each other and a solid surface. While a biofilm may contain microbial cells, it may also contain extracellular substances, such as proteins or polysaccharides, e.g., capsular polysaccharides expressed by the microbe.

Biofilms can be found in association with both low and high nutrient sources. Examples of biofilms are disclosed in Table 1 of Wimpenny, *Adv. Dent. Res.*, 11:150-159, 1997, which is incorporated by reference herein in its entirety. Biofilms include those found in association with high nutrient sources such as plant surfaces, e.g., rhizospheres, but also on inert surfaces such as contact lenses, prostheses, catheters, metal plates, joints, heart valves, and stents. Other sources of biofilms include animal surfaces, e.g., oral surfaces, including, e.g., the cheek, tongue, palate, epithelium, tooth surfaces, epithelia, such as the gut, rumen and vagina, and the surfaces of internal organs such as the lung and heart, and on heart valves.

When present in the oral cavity as subgingival biofilms, they are referred to as dental plaque. Dental plaque is involved in the development of conditions such as caries, periodontitis, dental implant failures, denture stomatitis, and oral yeast infections such as candidiasis.

Examples of biofilms associated with specific microbial infections include those formed in supragingival deposits by gram positive *Actinomycete* spp., especially *A. viscosus*. Gram-negative bacteria can also be found in association with supragingival biofilms. These bacteria include *P. gingivalis, F. nucleatum*, as well as coccobacilli and *Capnocytophage* spp.

Pathogens associated with non-oral biofilms include *P. aeroginosa*, which is found in the trachea of patients suffering from cystic fibrosis disease; *E. coli* biofilms found in infections associated with urinary tract and intestinal infections, and biofilms formed by *Staphylococcus* spp. in eye infections. The latter infections are frequently associated with contact lenses.

Biofilms can also be found in association with eukaryotic cells, e.g., cells specialized for secretion of extracellular matrix such as those described in Alberts et al., Molecular Biology of the Cell, 3rd Ed., 1994, at p. 1189. These cells include epithelial cells, e.g., ameloblasts, which secrete tooth enamel, the proteoglycan-secreting planum semilunatum cells of the vestibular apparatus of the ear, and the interdental cell of the organ of Corti, which secretes the tectorial membrane-covering hair cells of the organ of Corti. Other cells include nonepithelial cells such as fibroblasts, pericytes, nucleus pulposus cells of invertebral disc, cementoblast/odontocytes, chondrocytes of hyaline cartilage, fibrocartilage, or elastic cartilage, osteoblasts/osteocytes, and osteoprogenitor cells, which are the stem cells of osteoblasts. Other extracellular matrix-secreting cells include the hyalocytes of the vitreous body of the eye, and the stellate cell of the perilymphatic space of the ear.

The methods of the invention can be used to increase the permeability of these naturally occurring biofilms to allow compounds to pass into the biofilms and into the underlying cells and tissues.

Methods of Generating Stress Waves

The properties of stress waves are described generally in WO98/23325, which is incorporated herein by reference in its entirety.

Stress waves can be generated by various energy sources. For example, stress waves can be generated by ablation or thermoelastic expansion of an appropriate target material by a high energy optical source such as a laser (Doukas et al., *Physical Characteristics and Biological Effects of Laser-Induced Stress Waves*, Ultrasound in Med. & Biol., 22:151-164, 1996). When stress waves are generated by laser, they can be referred to as laser stress waves.

The laser beam can be generated by standard optical modulation techniques known in the art, e.g., Q-switched or mode-locked lasers using, for example, electro or acousto-optic devices. Standard commercially available lasers that can operate in a pulsed mode in the infrared, visible, and/or near infrared spectrum include Nd:YAG, Nd:YLF, $CO_2$, excimer, dye, Ti:sapphire, diode, holmium (and other rare-earth materials), and metal-vapor lasers. The pulse widths of these light sources are adjustable, and can vary from several tens of femtoseconds (fs) to several hundred microseconds.

For use in the new methods, the optical pulse width can vary from 100 fs to about 10 μs and is preferably between about 500 ps and 40 ns.

Stress waves can also be generated by extracorporeal lithotripters (one example is described in Coleman et al., Ultrasound Med. Biol., 15:213-227, 1989). These stress waves have rise times of 30 to 450 ns, which is longer than laser-generated stress waves.

The type of lithotripter used is not critical, as long as it is capable of generating stress waves. Thus, either electrohydraulic, electromagnetic, or piezoelectric lithotripters can be used.

Stress waves can also be generated using transducers, such as piezoelectric transducers. Preferably, the transducer is in direct contact with the coupling medium, and undergoes rapid displacement following application of an optical, thermal, or electric field to generate the stress wave.

For example, dielectric breakdown can be used, and is typically induced by a high-voltage spark (similar to those used in certain extracorporeal lithotripters; see e.g., Coleman et al., Ultrasound Med. Biol., 15:213-227, 1989). In the case of a piezoelectric transducer, the transducer undergoes rapid expansion following application of an electrical field to cause a rapid displacement in the coupling medium.

Stress waves can alternatively be generated by inducing explosive reactions in energetic materials such as those described in Kodama et al., Ultrasound Med. Biol. 24:1459 (1998). Useful energetic materials include nitrocellulose (NC), glacidy azide polymer (GAP), bis-azidomethyloxetane polymer (BAMO), azidomethyl methyloxetane polymer (AMMO), and silver azide.

For some applications it is desirable to generate stress waves with the aid of fiber optics. Fiber optic delivery systems are particularly maneuverable and can be used to irradiate target materials located adjacent to biofilms to generate stress waves in remote, otherwise inaccessible locations. These types of delivery systems, when optically coupled to lasers, for example, are preferred as they can be integrated into catheters and related flexible devices, and used to irradiate most organs in the human body. In addition, to launch a stress wave having the desired rise times and peak stress, the wavelength of the optical source can be easily tailored to generate the appropriate absorption in a particular target material, which then emits the stress waves.

When the stress wave is generated by irradiation of a target material, the absorbing target material acts as an optically triggered transducer. Following absorption of light, the target material undergoes rapid thermal expansion, or is ablated, to launch a stress wave. Typically, metal and polymer films have high absorption coefficients in the visible and ultraviolet spectral regions.

Many types of materials can be used as the target material in conjunction with a laser beam, provided they fully absorb light at the wavelength of the laser used. The target material may be present as part of a container and can be composed of a metal such as aluminum or copper; a plastic, such as polystyrene, e.g., black polystyrene; a ceramic; or a highly concentrated dye solution. The target material must have dimensions larger than the cross-sectional area of the applied laser energy. In addition, the target material must be thicker than the optical penetration depth of the laser into the target so that no light passes through to strike the surface of the biofilm or underlying tissue. When the target material is present as part of a container, it must also be sufficiently thick to provide mechanical support. When the target material is made of a metal, the typical thickness will be 1/32 to 1/16 inch, i.e., a metal foil. For plastic target materials, the thickness will be generally 1/16 to 1/8 inch.

The target material must be coupled to the biofilm by a coupling medium. A coupling medium is a liquid, gel, or cream medium in which the stress waves are propagated. The coupling medium enables a direct contact of the stress wave to the surface of the biofilm layer and minimizes acoustic reflections. In many applications the solution or gel in which the compound to be delivered is dissolved or suspended may itself act as the coupling medium. Alternatively, a coupling medium can be used during application of the stress waves, and then, if desired, removed to apply the compound to the now permeabilized biofilm. Thus, a solution containing the compound to be delivered, e.g., water, oil, such as castor oil, an isotonic medium such as phosphate buffered saline (PBS), or a gel such as a collagenous gel, can all be used as the coupling medium.

When using an extracorporeal lithotripter, a stress wave of the appropriate rise time can be generated by propagating in a non-linear coupling medium (e.g., water) for a distance determined as described in WO98/23325.

The compound to be delivered is thoroughly dispersed in, and is preferably dissolved in, the coupling medium. Thus, hydrophilic compounds can be mixed with an aqueous coupling medium (e.g., water, solutions of surfactants, such as sodium lauryl sulfate (SLS), benzalkonium chloride (BAC), cocoamidopropyl betaine (CAPB)), and hydrophobic compounds can be mixed with an oil-based coupling medium (such as castor oil). These agents also enhance the coupling ability of the medium.

The coupling medium can in addition include a surfactant that enhances transport of the compound to be delivered, e.g., by prolonging the period of time in which the biofilm remains permeable to the compound following the generation of a stress wave. The surfactant can be, e.g., an ionic or nonionic detergent and thus can include, e.g., sodium lauryl sulfate, cetyl trimethyl ammonium bromide, and lauryl dimethyl amine oxide.

Stress wave characteristics can be measured using methods standard in the art. For example, peak stress or pressure, and rise time can be measured using a polyvinylidene fluoride (PVDF) transducer method as described in Doukas et al., Ultrasound Med. Biol., 21:961 (1995).

A useful parameter by which to assess the efficiency of generation of the stress wave is the coupling coefficient ($C_m$), which is defined as the total momentum transfer to the target material during ablation divided by the pulse energy. The efficiency of conversion of laser energy to mechanical energy of the stress wave is given by the coupling coefficient of the target material.

The permeabilizing effects of stress waves can be enhanced using confined ablation. In confined ablation, a laser beam-transparent material, such as a quartz optical window, or glass, is placed in close contact with the target material. Confinement of the plasma created by ablating the target material by using the transparent material increases the coupling coefficient by an order of magnitude (Fabro et al., *J. Appl. Phys.*, 68:775, 1990). The transparent material can be quartz, glass, or transparent plastic. Since voids between the target material and the confining transparent material allow the plasma to expand, thereby decreasing the momentum imparted to the target, the transparent material is preferably bonded to the target material using an initially liquid adhesive, such as carbon-containing epoxies, to prevent such voids.

Since the effects induced by the stress waves last for several minutes, the transport rate of a drug diffusing passively through the biofilm along its concentration gradient can be increased by applying hydrostatic pressure on the surface of the biofilm following application of the stress wave. The hydrostatic medium can be any liquid, such as water or phosphate buffered saline.

Compounds

Because stress waves exert physical forces to increase the permeability of the biofilm, they can be used to transport many different types of compounds. Thus, the compounds can be bioactive agents such as photosensitizing agents, e.g., benzoporpherene derivative monoacid ring A (BPD-MA); antibiotics, such as metronidazole and minocycline, and antiseptics, such as chlorhexidine and triclosan.

Additional bioactive compounds which can be used include therapeutic agents such as chemotherapeutics, e.g., cisplatin, polypeptides, including growth factors and antibodies, and nucleic acids, such as oligonucleotides, DNA, RNA, and plasmids, local anesthetics, such as lidocaine and benzocaine. The compounds may optionally be heated prior to generation of the stress wave to facilitate their transport into the biofilms.

In general, differential drug localization can be achieved using guidelines for administration determined using standard techniques known in the field of pharmacology. Preferably, the compound dosage and time course are such that a 2:1 or greater concentration ratio is achieved in the treated tissues, cells, or other treated sites, compared to the surrounding, untreated tissues or sites.

Determining the appropriate dosage for a specific compound, and for a particular subject or patient (human or animal) is a routine matter for one skilled in the art of pharmaceutical administration. Two approaches are commonly used to assay directly the quantity of drug in the diseased (treated) and surrounding sites. First, tissue samples are obtained from animals (e.g., pigs) or patients who have been treated with different dosage and timing protocols. The quantity of drug in each sample is then measured either chemically, or if there is a unique optical signal such as fluorescence, then by quantitative microscopy or laser-induced fluorescence. The results are tabulated to determine a scale of optimum drug dosages and types of stress waves for a given biofilm, the structure attached to the biofilm, and the compound.

Compounds which have a toxic effect at higher dosages can be administered to a patient using guidelines for administration that will produce greater concentrations of the drugs in the treated tissues or cells compared to the surrounding tissues, while maintaining adequate levels of the drug in these treated tissues or cells.

Topical application and delivery of compounds by the new methods allow the compounds to be localized to a site of interest. Thus, the compound, e.g., a drug, is more concentrated at the site of action and has a minimal, if any, systemic concentration. This enhances the therapeutic effect of the drug and simultaneously minimizes systemic side effects. Another advantage compared to systemic administration is that compounds transported through biofilms bypass systemic deactivation or degradation (e.g., hepatic "first-pass" effects). Gastrointestinal incompatibility and potential toxicological risks are also minimized relative to systemic administration. In addition, drugs developed for topical application can be designed so that they are deactivated systematically (i.e., the "soft drug" concept), using standard techniques. Topical administration may also be desired when the compound is rare or expensive.

EXAMPLES

The invention will be further described in the following examples, which do not limit the scope of the invention described in the claims.

Example 1

Stress Waves Enhance the Penetration of Methylene Blue in *A. Viscosus* Biofilms The ability of stress waves to enhance penetration of a compound into a biofilm was demonstrated by comparing the penetration of methylene blue into a biofilm in the presence and absence of an applied laser stress wave.

The biofilm was generated by culturing *A. viscous* on an enamel surface. Enamel surfaces measuring 5×5×2 mm were sterilized and suspended in trypticase soy agar with 5% sheep blood in wells of 24-well plates with cultures of *A. viscosus*. Plates containing the suspended enamel surfaces were incubated in an anaerobic chamber at 35° C. Fresh medium containing *A. viscosus* cultures was added twice per week until a 1.0-1.5 mm thick biofilm was formed.

Specimens were incubated with methylene blue (Sigma, St. Louis, Mo.), followed by exposure to a laser pulse, or incubated with methylene blue only for 5 minutes in the absence of light.

Specimens to be exposed to a laser pulse were placed in a reservoir as shown in FIG. 1. A reservoir 10 contained the enamel surface 12, to which the *A. viscosus* biofilm 14 was adhered. The biofilm 14 was bathed in a solution 16 containing 50 µg/ml methylene blue for 5 minutes, after which a sterile black plastic (unexpanded polystyrene) target 18 (1 cm in diameter and 1 mm thick) was placed over the top of the reservoir 10 in contact with the solution 16. Biofilms were exposed to a single laser pulse 20, which, after ablating the target 18 generated a stress wave 22 through the solution 16. The laser pulse was generated with a Q-switched ruby laser (not shown). The operating parameters of the laser were 694 nm, 2.1 J, and 23 ns pulse duration.

Figure 2:
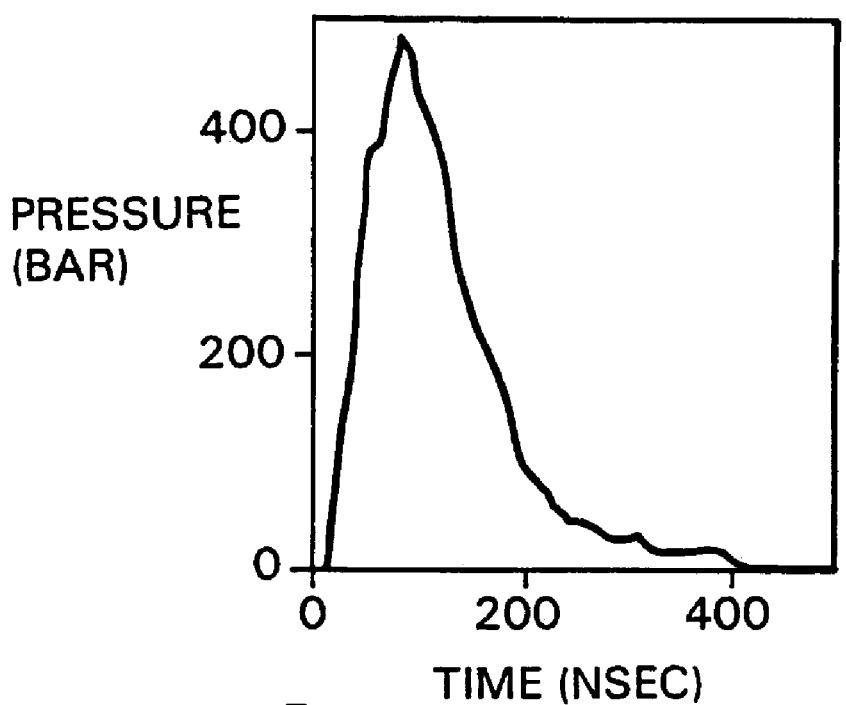
FIG. 2 is a graph illustrating the waveform of a stress wave generated by the ablation of a black polystyrene target material with a single 23 ns Q-switched ruby laser pulse.

The temporal waveform of a stress wave generated by ablation of the polystyrene target by 694 nm radiation from the Q-switched laser is shown FIG. 2. The stress wave was measured by a calibrated piezoelectric transducer and had a rise time of 50 nsec, 110 nsec duration, and peak pressure of 600 bar. The beam size was about 6 mm in diameter and provided a fluence of about 7.0 J/cm$^2$.

The specimens were then placed in petri dishes, covered with PBS, after which biofilms were viewed with a Leica TCS NT™ fluorescence scanning confocal microscope. The microscope was equipped with a 10× water immersion objective lens. An argon laser (476 nm) was used as the excitation source for methylene blue. Sections were collected at 100 µm intervals and analyzed by image-processing to assess the distribution of methylene blue within the biofilm matrices.

The images demonstrated that the fluorescence from the biofilm where laser-generated stress waves were applied was much stronger than the control, indicating that the methylene blue had penetrated into the biofilm. In addition, the fluorescent intensity of a control slice was increased to a depth of no more than 400 µm, whereas florescence was observed to a depth of 600-700 µm in the specimens subjected to stress waves. A significant increase of fluorescence intensity obtained from the specimens exposed to stress waves was observed as compared to controls.

These results demonstrate that application of stress waves to a biofilm facilitates penetration of the biofilm with a bioactive agent.

Example 2

Stress Waves Enhance Bactericidal Effects of a Photosensitizer on Bacterial Biofilms To demonstrate that stress waves can enhance the bacteriocidal effects of photosensitizing agents on biofilms, 4. viscosus biofilms were exposed to methylene blue, which exerts phototoxic effects upon exposure to light.

The biofilms were grown on enamel surfaces as described in Example 1. Biofilms were incubated with methylene blue for 1 or 5 minutes and exposed to stress waves (one pulse), after which they were exposed to 666 nm red light with a fluence of 15 J/cm$^2$ at an irradiance of 50 mW/cm$^2$. In control samples, biofilms were treated only with methylene blue, or were treated with methylene blue and exposed to red light, but without stress waves. An argon ion laser with an emission of 514.5. nm was used to pump a dye laser. The laser light was coupled into a 1.0 mm quartz fiber and appropriate spot sizes were created with an objective lens.

After illumination, adherent bacteria from the samples as treated above were scraped from the enamel surfaces with a sterile blade and dispersed in trypticase soy broth. Serial dilutions were prepared, and 100 µl aliquots were spread over the surfaces of blood agar plates. Survival fractions from each biofilm were calculated by counting the colonies on the plates and dividing by the number of colonies from dark controls incubated with the drug and kept at room temperature for periods equal to irradiation time. Other controls were: 1) biofilms untreated with methylene blue, light, or stress waves; 2) biofilms exposed only to a stress wave; 3) biofilms exposed to light without methylene blue; and 4) biofilms exposed to light after incubation with methylene blue.

Figure 3:
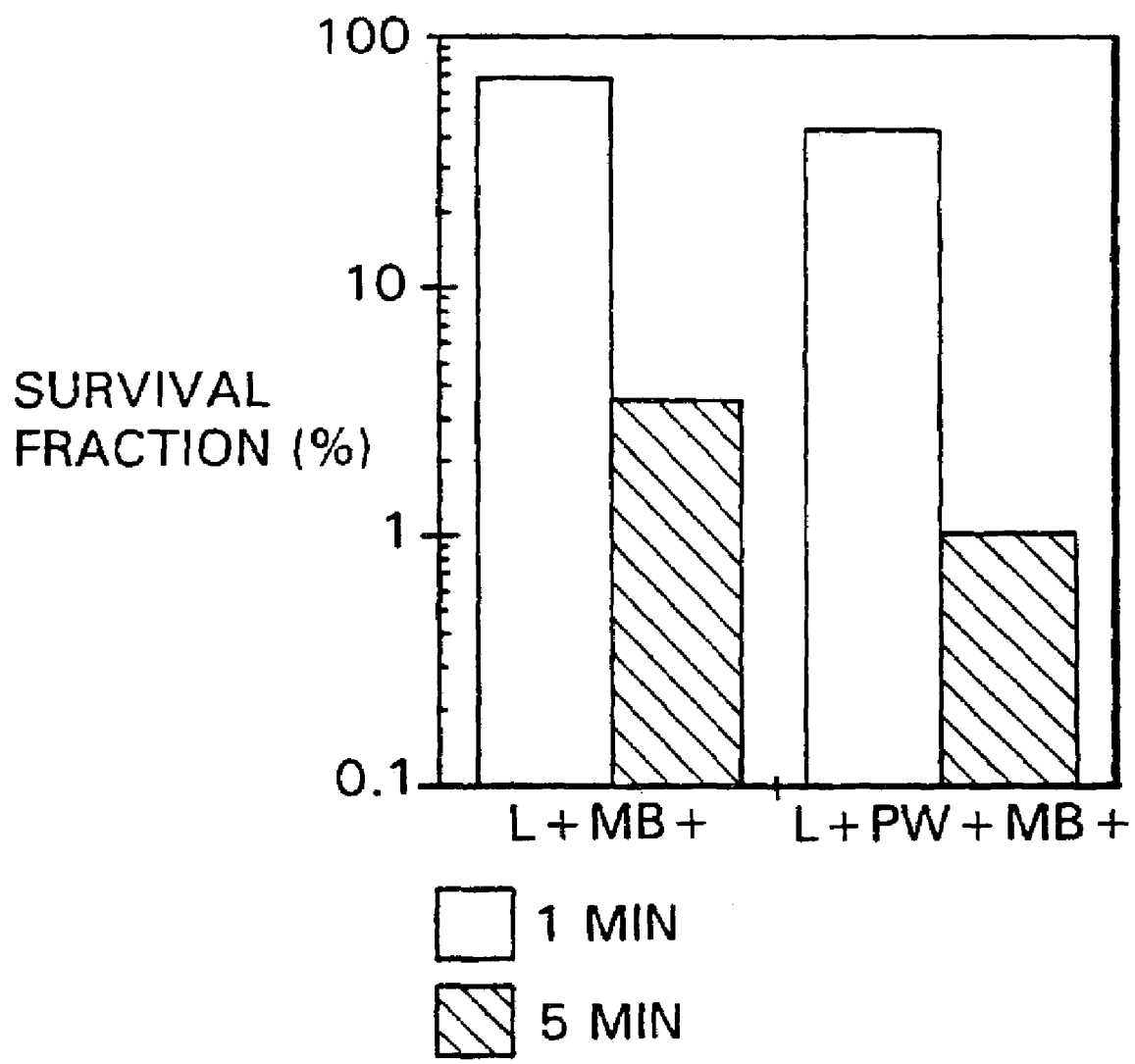
FIG. 3 is a graph illustrating the phototoxicity of *A. viscosus* in biofilms after incubation with 50 μg/ml methylene blue (MB) for 1 minute (white bar) and 5 minutes (hatched bar) followed by the application of a single pressure wave and red light (L+MB+PW) or light only (L+MB).

As shown in FIG. 3, 99% of the bacteria associated with biofilms were killed when subjected to a stress wave and red light after a five-minute incubation with methylene blue, whereas only 57% of control bacteria were killed after exposure to red light in the absence of an applied stress wave. In addition, a one-minute incubation in methylene blue followed by a stress wave killed 96.5% of bacteria whereas the same conditions without a stress wave killed only 34% of bacteria. These results demonstrate that application of a photosensitizer along with stress waves to a biofilm enhances the phototoxic effect of the photosensitizer.

Example 3

Delivery of Bioactive Agents into Biofilms in Periodontal Pockets

A solution of metronidazole is applied to a periodontal pocket of a patient with chronic destructive periodontitis. Stress waves generated by ablation of a polystyrene target material with a Q-switched ruby laser are used to permeabilize biofilms (dental plaque) attached to the tooth root.

A stainless steel needle (0.8 mm inner diameter by 1.3 mm outer diameter) is used as a hollow waveguide. To deliver the laser pulse to the target, the blunt end of the needle is sealed with the target that absorbs the laser pulse. The target is chosen so that it absorbs the laser pulse completely.

Upon delivery of the laser pulse, the target emits a stress wave that temporarily increases the permeability of the biofilm. As a result, the metronidazole passes into the biofilm, thereby facilitating metronidazole-mediated destruction of cells in the biofilm.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of delivering a compound into a matrix of a biofilm, the method comprising:
   (a) contacting the biofilm with the compound and a coupling medium;
   (b) contacting the coupling medium with a target; and
   (c) causing the target to propagate a sufficient number of stress waves into the biofilm to increase the permeability of the biofilm, thereby enabling the compound to pass into the matrix of the biofilm.

2. The method of claim 1, wherein at least one of the stress waves is a broad-band compressive wave having a rise time of at least 500 ps and a peak pressure of at least 50 bar.

3. The method of claim 1, wherein the stress wave has a peak pressure of 550-650 bar.

4. The method of claim 1, wherein the stress wave has a rise time of about 10-100 ns.

5. The method of claim 1, wherein the stress wave is generated by exposing the target material to a pulsed laser beam.

6. The method of claim 5, wherein the laser beam has a wavelength between about 140 nm and about 12 µm.

7. The method of claim 5, wherein a transparent material is bonded to a surface of the target material.

8. The method of claim 5, wherein the target material is selected from a group consisting of a metal foil, a plastic, and an energetic material.

9. The method of claim 8, wherein the metal foil comprises a metal selected from a group consisting of aluminum and copper.

10. The method of claim 5, wherein the target material comprises a polymer.

11. The method of claim 5, wherein the target material comprises polystyrene.

12. The method of claim 5, wherein the target material comprises a material that absorbs laser energy, and wherein the stress wave is generated by laser-induced heating of the absorbing material.

13. The method of claim 1, wherein the compound comprises an antimicrobial agent.

14. The method of claim 1, wherein the biofilm comprises one or more bacteria or products thereof.

15. The method of claim 1, wherein the biofilm comprises one or more bacterial capsular polysaccharides.

16. The method of claim 1, wherein the biofilm comprises a microorganism or product thereof selected from the group consisting of an *Actinomycete* spp. or a product thereof, *A. viscosus* or a product thereof, or *P. gingivalis* or a product thereof.

17. The method of claim 1, wherein the biofilm comprises one or more fungi or products thereof.

18. The method of claim 1, wherein the biofilm comprises one or more protozoa or products thereof.

19. The method of claim 1, wherein the compound and the coupling medium is provided in a reservoir, wherein the reservoir is arranged to enable the coupling medium to directly contact a surface of the biofilm.

20. The method of claim 19, wherein the coupling medium further comprises a surfactant.

21. The method of claim 20, wherein the surfactant is sodium lauryl sulfate.

22. The method of claim 1, wherein the biofilm contacts an enamel surface, a periodontal pocket, a tracheal surface, or an internal organ surface of a mammal.

23. The method of claim 22, wherein the mammal is a human.

24. The method of claim 1, wherein the compound comprises an antimicrobial agent, and wherein the agent is delivered into the matrix of the biofilm by contacting the biofilm with the antimicrobial agent, and exposing the target material disposed on the biofilm to a pulsed laser beam, thereby propagating one or more stress waves through the biofilm contacting the antimicrobial agent, thereby causing the antimicrobial agent to enter the matrix.

25. A method of treating disorders associated with a biofilm, the method comprising exposing a target coupled to the biofilm via a coupling medium to one or more stress waves sufficient to propagate into and permeabilize the biofilm, and then delivering a therapeutic agent into a matrix of the biofilm, thereby treating the disorder associated with the biofilm.

26. The method of claim 25, wherein the therapeutic agent comprises an antimicrobial agent.

* * * * *